United States Patent [19]

Hojo et al.

[11] Patent Number: 4,785,119

[45] Date of Patent: Nov. 15, 1988

[54] 3-AMINOPYRROLIDINE COMPOUND AND PROCESS FOR PREPARATION THEREOF

[75] Inventors: Kou Hojo, Ageo; Anji Sakamoto, Fukaya; Masumi Tsutsumi, Maebashi; Tamotsu Yamada, Fujioka; Kazuhiko Nakazono, Fukaya; Kazuya Ishimori, Yokohama, all of Japan

[73] Assignee: Tokyo Kasei Kogyo Co., Ltd., Tokyo, Japan

[21] Appl. No.: 916,936

[22] Filed: Oct. 7, 1986

[30] Foreign Application Priority Data

Oct. 11, 1985 [JP] Japan .................................. 60-226041
Oct. 11, 1985 [JP] Japan .................................. 60-226042
Aug. 8, 1986 [JP] Japan .................................. 61-186607

[51] Int. Cl.$^4$ ............................................ C07D 207/14
[52] U.S. Cl. ...................................... 548/557; 548/559
[58] Field of Search ................................. 548/557, 559

[56] References Cited

U.S. PATENT DOCUMENTS

| | | | |
|---|---|---|---|
| 3,424,760 | 1/1969 | Helsley et al. ...................... | 548/557 |
| 3,424,761 | 1/1969 | Helsley et al. ...................... | 548/557 |
| 3,424,762 | 1/1969 | Helsley ............................... | 548/557 |
| 3,433,801 | 3/1969 | Dawson .............................. | 548/557 |
| 3,433,802 | 3/1969 | Dawson et al. ..................... | 548/557 |
| 3,509,171 | 4/1970 | Welstead, Jr. et al. ........ | 548/557 X |
| 3,549,658 | 12/1970 | Helsley ............................... | 548/557 |
| 3,577,440 | 5/1971 | Lunsford et al. ................... | 548/557 |
| 4,056,535 | 11/1977 | Henry et al. ........................ | 548/557 |

FOREIGN PATENT DOCUMENTS 2500833 9/1982 France .

*Primary Examiner*—Joseph Paul Brust
*Attorney, Agent, or Firm*—Birch, Stewart, Kolasch & Birch

[57] ABSTRACT

Disclosed is a novel compound of 3-aminopyrrolidine having the formula (I):

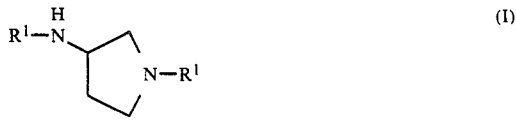

in which R$^1$ is hydrogen, an alkyl, an aralkyl or an aryl.

5 Claims, No Drawings

3-AMINOPYRROLIDINE COMPOUND AND PROCESS FOR PREPARATION THEREOF

This invention relates to 3-aminopyrrolidines and to a process for preparing the same. More particularly, it relates to 3-aminopyrrolidines having the general formula:

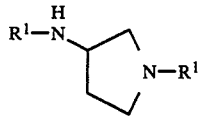

wherein $R^1$ is a member selected from the group consisting of a hydrogen atom, and alkyl, aralkyl, and aryl radicals.

One object of the present invention is to provide novel parent 3-aminopyrrolidine and N,N'-disubstituted 3-aminopyrrolidines, and salts thereof, which are useful as starting materials, and as building blocks for construction of useful products in chemical, pharmaceutical, and agricultural industries. In particular, some 3-aminopyrrolidine derivatives have been used recently in making particular antibacterial agents, which showed striking activities (J. Matsumoto et al., J. Med. Chem., 27, 1543(1984)).

The another object of the present invention is to provide a novel and general process for the production of parent 3-aminopyrrolidine and N,N'-disubstituted 3-aminopyrrolidines, and salts thereof.

STATEMENT OF PRIOR ARTS

C. D. Lunsford and coworkers reported in 1967~1968 the synthesis of some N,N'-substituted 3-aminopyrrolidines by the reaction of primary or secondary amines with 1-substituted 3-chloropyrrolidines or 1-substituted 3-tosyloxypyrrolidines, which had been prepared from 1-substituted 3-pyrrolidinol. These N,N'-substituted 3-aminopyrrolidines were used in making a number of aminoalkylindols, which showed a significant central nervous system depressant activity [C. D. Lunsford et al., J. Med. Chem., 10, 1015(1967); ibid., 11, 1034(1968), U.S. Pat. No. 2,830,997].

SUMMARY OF THE INVENTION

The invention provides a 3-aminopyrrolidine compound and a process for preparation thereof. In particular it provides a compound of 3-aminopyrrolidine having the formula (I):

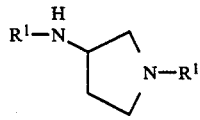 (I)

in which $R^1$ is hydrogen, an alkyl, an aralkyl or an aryl.

The present invention compound includes one in which $R^1$ in the formula (I) is hydrogen and another compound in which $R^1$ in the formula is an alkyl having 1 to 20 carbon atoms, preferably 1 to 3 carbon atoms, an aralkyl having 1 or 2 carbon atoms in the alkylene and 1 or 2 phenyl rings or a phenyl which may have a substituent such as methyl, methoxy, a halogen and nitro. In the latter group, $R^1$ preferably is methyl, ethyl, benzyl or phenyl.

The present invention provides a process for preparing a compound as defined above which comprises reacting 1,2,4-trisubstituted butane having the formula (II):

$$XCH_2CHYCH_2CH_2Z \quad (II)$$

in which X, Y and Z each are a halogen or OR, R being an alkylsulfonyl or an arylsulfonyl, with a primary amine having the formula (III): $R^1NH_2$ in which $R^1$ is defined above. It is preferably that R is an alkylsulfonyl having 1 to 6 carbon atoms in the alkyl or an arylsulfonyl such as phenylsulfonyl which may have a substituent on the phenyl portion such as methyl, methoxy, a halogen and nitro.

The above shown process provides an intermediate compound having the formula (I) in which $R^1$ is an aralkyl or a salt thereof with a protonic acid. The intermediate compound may be catalytically hydrogenated to produce 3-aminopyrrolidine. The intermediate compound preferably includes one in which $R^1$ has the formula (IV): $R^2R^3CH$ in which $R^2$ is phenyl or a substituted phenyl and $R^3$ is hydrogen, an alkyl or phenyl. The phenyl for $R^2$ may be substituted by methyl, methoxy, a halogen or nitro.

According to the present invention, novel 3-aminopyrrolidines represented by the general formula:

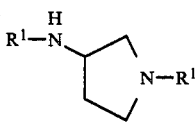

can be obtained in one step by the reaction of 1,2,4-trisubstituted butanes, represented by the general formula:

$$XCH_2CHYCH_2CH_2Z$$

wherein X, Y, and Z represent a halogen atom or OR group in which R is either an alkane sulfonyl or aromatic sulfonyl radical, with primary amines represented by the general formula:

$$R^1NH_2$$

wherein $R^1$ is a member selected from the group consisting of a hydrogen atom, an alkyl radical having 1 to 20 carbon atoms, an aralkyl radical comprising benzyl, α-phenethyl, or diphenylmethyl radical with or without substituents on the aliphatic carbon and/or on the benzene ring, and a phenyl radical with or without substituents on the benzene ring.

A number of N,N'-disubstituted 3-aminopyrrolidines can be prepared by the method of the present invention. As examples of such compounds, one can mention parent 3-aminopyrrolidine, N,N'-dimethyl-3-aminopyrrolidine, N,N'-diethyl-3-aminopyrrolidine, N,N'-dibenzyl-3-aminopyrrolidine, and N,N'-diphenyl-3-amino-pyrrolidine.

Alternatively, parent 3-aminopyrrolidine is also prepared according to the present invention by catalytic hydrogenation of N,N'-disubstituted-3-aminopyrrolidines represented by the general formula:

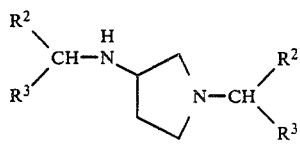

which are prepared by the reaction of the 1,2,4-trisubstituted butanes defined above, with primary amines having the general formula:

$R^2(R^3)CHNH_2$, wherein $R^2$ is a phenyl or substituted phenyl radical, and $R^3$ is a member selected from the group consisting of a hydrogen atom, an alkyl radical having 1 to 4 carbon atoms, and phenyl or substituted phenyl radical. As examples of such N,N'-disubstituted 3-aminopyrrolidines, one can mention N,N'-dibenzyl-3-aminopyrrolidine, N,N'-bis(1-phenethyl)-3-aminopyrrolidine, and N,N'-bis(diphenylmethyl)-3-aminopyrrolidine.

The process of the present invention is explained in details. As 1,2,4-trisubstituted butanes that can be used in the process of the present invention, following compounds can be mentioned for instance; 1,2,4-trichlorobutane, 1,2,4-tribromobutane, 1,4-dibromo-2-methanesulfonoxybutane, 1,2-dibromo-4-chlorobutane, 1,2,4-tris(methanesulfonoxy)butane, 1,2,4-tris(p-toluenesulfonoxy)butane, and 3,4-dibromo-1-methanesulfonoxybutane. These 1,2,4-trisubstituted butanes can be readily prepared starting from comercially available compounds like 1,2,4-butanetriol, 3-butene-1-ol, 4-chloro-1-butene, and 4-bromo-1-butene by conventional methods in the art.

According to the present invention, 3-aminopyrrolidines that have two identical substituents on nitrogen atoms at 1- and 3-positions, can be prepared by simply treating 1,2,4-trisubstituted butanes with primary amines. This type of reaction is so simple that one can perform under a variety of reaction conditions, in the presence or absence of another base and solvent. In any case, it is preferable to employ sufficient amounts of primary amines (more than 3 equivalents), and reaction temperature of 40° to 150° C.

As the base, ordinary alkalis like metal hydroxides, metal carbonates, and metal alkoxides are preferable; a primary amine that is to be introduced into a pyrrolidine ring system can be employed as well.

The reaction of the present invention can be performed in a homogeneous system using ordinary solvents like water, ethanol, isopropyl alcohol, benzene, and toluene. The reaction can also be carried out in a heterogeneous two phase system using organic solvents and aqueous alkalis.

Parent 3-aminopyrrolidine can be prepared according to the present invention by treatment of trisubstituted butanes with ammonia, preferably being performed in an autoclave. The reaction can be carried out in organic solvents, in water, or in liquid ammonia. Use of large excess of ammonia is essential; preferably 20~80 times moles of ammonia to that of trisubstituted butanes is used. The reaction temperature of 20°-120° C., and the reaction period of 1~20 hr are usually employed depending on the reactivities of trisubstituted butanes.

Parent 3-aminopyrrolidine or its protonic acid salts can be conveniently prepared by catalytic hydrogenation of the corresponding N,N'-disubstituted 3-aminopyrrolidines or its protonic acid salts, which have two identical substituents that can be removed by reduction. Catalytic hydrogenations of N,N'-substituted 3-aminopyrrolidines is usually carried out in an autoclave in ordinary solvents like water, methanol, ethanol, isopropyl alcohol, tetrahydrofuran, dioxane, dimethoxyethane, and acetic acid. The reduction proceeds in a single or mixed solvent system. Catalysts like Pd—C, Pd—BaSO$_4$, PdO, and PtO$_2$ are preferable and these can be used as much as 5 to 20% weight of the starting material employed. Reductions are usually carried out at temperature 20° to 150° C. under the hydrogen pressure of 1 to 30 kg/cm$^2$, and are completed in 2 to 12 hours.

In general, catalytic hydrogenations of protonic acid salts of substituted 3-aminopyrrolidines proceed under milder conditions and give better yields than the case in which free N-substituted 3-aminopyrrolidines are employed.

Therefore, when needed, it is advantageous to carry out the reduction of N-substituted 3-aminopyrrolidines in the form of its protonic acid salts.

The process of the present invention is described in more detail with reference to the following examples, which are however to be construed for the purpose of illustration and not for the limitation.

EXAMPLE 1

3-Aminopyrrolidine

Liquid ammonia (370 g) is introduced at room temperature into an autoclave which contained 1,2,4-tribromobutane (88 g, bp 99.5° C./5.5 mmHg). The mixture is stirred for 20 hr at 45°~50° C. under the pressure of 70 kg/cm$^2$. After completion of reaction, excess ammonia is evaporated, and water (300 ml) and then sodium hydroxide (72 g) are added to the residue. 3-Aminopyrrolidine is co-distilled with water. To the distillate is added concd hydrochloric acid (50 ml) and the solution is concentrated to dryness to give crude 3-aminopyrrolidine dihydrochloride (18.9 g, 39.8%). This is added to methanol (80 ml) solution of sodium methoxide (13.2 g), and precipitated sodium chloride is filtered. Distillation of the filtrate under the atmosphere of nitrogen gave 3-aminopyrrolidine 8.1 g (31.7%) which boiled at 159°~160° C.

$n_D^{20}$ 1.4897. $SG_{20}^{20}$ 0.9910.

NMR (CDCl$_3$) $\delta$ = 3.30~3.70 (m, 2H), 2.43~3.23 (m, 4H), 1.13~2.26 (m, 2H), 1.50 (s, 3H).

IR (neat) 3250, 1600, 870 cm$^{-1}$ (—NH$_2$).

Solubility

Freely soluble in water, ethanol, diethyl ether, tetrahydrofuran, dioxane, acetonitrile, chloroform, carbon tetrachloride, benzene. Soluble in hexane.

Derivatives

3-Aminopyrrolidine dihydrochloride

NMR (DMSO-d$_6$) $\delta$ = 8.33~10.10 (s, broad, 5H), 3.66~4.23 (m, 1H), 2.93~3.66 (m, 4H), 1.93~2.50 (m, 2H).

IR (KBr) 3200~2800, 1590~1550 cm$^{-1}$ (NH$_3^+$).

Chlorine content (C$_4$H$_{12}$N$_2$Cl$_2$): Calcd. (%) 44.58; Found (%) 43.35.

N,N'-Diacetyl-3-aminopyrrolidine

NMR (CDCl$_3$) δ=7.00~7.40 (s, broad, 1H), 4.17~4.73 (m, 1H), 3.13~3.90 (m, 4H), 1.77~2.47 (m, 8H).

IR (neat) 3400~3250, 1670~1620, 1550 cm$^{-1}$.

EXAMPLE 2

N,N'-Dimethyl-3-aminopyrrolidine 1,2,4-Tris(methanesulfonoxy)butane (170.2 g, mp 63.5°~64.5° C.) is added to 40 (w/w)% aqueous solution of methylamine (863 ml). The mixture is gradually heated with stirring to 84°~94° C. and kept at this temperature for 2.5 hr.

The reaction mixture is concentrated, and sodium hydroxide (200 g) in water (400 ml) added to the residue. The mixture is shaken with benzene (2×300 ml), and combined benzene layers are dried over magnesium sulfate, and concentrated at an atmospheric pressure. The crude material (50.7 g, 88.8%) was purified by distillation through a Vigreux column (20 cm) under a nitrogen atmosphere to give N,N'-dimethyl-3-aminopyrrolidine (26.8 g, 46.9%), which boiled at 148°~149° C.

$n_D^{20}$ 1.4562. $SG_{20}^{20}$ 0.8824.

NMR (CDCl$_3$) δ=3.07~3.40 (m, 1H), 2.40 (s, 3H), 2.37 (s, 3H), 1.33~2.83 (m, 7H).

IR (neat) 3250 cm$^{-1}$.

EXAMPLE 3

N,N'-Diethyl-3-aminopyrrolidine 1,2,4-Tribromobutane (294.9 g, bp 99.5° C./5.5 mmHg) is added to 70 (w/w)% aqueous solution of ethylamine (1600 ml).

The mixture is gradually heated with stirring to 83°~85° C. and kept at this temperature for 1.5 hr. The reaction mixture is concentrated, and sodium hydroxide (400 g) in water (800 ml) added to the residue. The mixture is shaken with benzene (2×300 ml), and combined benzene layers are dried over magnesium sulfate. It is concentrated at an atmospheric pressure and crude N,N'-diethyl-3-aminopyrrolidine (114.1 g, 80.2%) is distilled under a nitrogen atmosphere.

Yield 77.5 g (54.5%). bp 178°-182° C.

This product is further purified in the form of its hydrochloric acid salt as follows: the product is added dropwise to the stirred solution of hydrogen chloride (41.7 g) in ethanol (180 ml). N,N'-Diethyl-3-aminopyrrolidine dihydrochloride precipitated, which is collected and recrystalized from ethanol (150 ml). White crystalline (88.0 g, 77.1%, mp 170°~172° C., chlorine content: found 32.88%, calcd. 32.96%) is obtained, which is then added portionwise to sodium methoxide (44.1 g) in methanol (200 ml) and heated to reflux for 30 min. Sodium chloride is removed by filtration, and a filtrate concentrated at an atmospheric pressure. Distillation of a residual liquid under a nitrogen atmosphere gave N,N'-diethyl-3-aminopyrrolidine (41.8 g, 71.8%) which boiled at 180°-182° C.

$n_D^{20}$ 1.4553.

NMR (CDCl$_3$) δ=3.10~3.46 (m, 1H), 1.30~2.90 (m, 11H), 1.10 (t, J=6 Hz, 6H).

IR (neat) 3200 cm$^{-1}$.

EXAMPLE 4

N,N'-Diphenyl-3-aminopyrrolidine

To a mixture of aniline (27.3 ml) and sodium hydroxide (6 g) in water (15 ml), is added with stirring 1,2,4-tribromobutane (14.7 g, bp 99.5° C./5.5 mmHg). The mixture is gradually heated to 100° C. and maintained at this temperature for 3 hr. and then cooled. Benzene (30 ml) and water (10 ml) are added, and the mixture is shaken. Organic layer is separated, washed with water, dried over sodium sulfate, and concentrated. Excess aniline is removed by distillation under reduced pressure (36°~39° C./1 mmHg). The residual liquid (10.3 g, 86.4%) is distilled to give N,N'-diphenyl-3-aminopyrrolidine (8.4 g, 70.7%) which boiled at 193°~194° C./1 mmHg, and solidified at room temperature. The solid melted at 68°~70° C. and also showed melting point of 68°~70° C. after being recrystallized from ethanol.

NMR (CDCl$_3$) δ=6.43~7.47 (m, 10H), 4.00~4.37 (m, 1H), 3.03~3.80 (m, 5H), 1.67~2.57 (m, 2H).

IR (neat) 3350, 1595 cm$^{-1}$.

EXAMPLE 5

N,N'-Dibenzyl-3-aminopyrrolidine and 3-aminopyrrolidine (a). To a mixture of benzylamine (192.9 g) and sodium hydroxide (36 g) in water (36 ml) is added with stirring 1,2,4-tribromobutane (88.4 g, bp 99.5° C./5.5 mmHg) in 5 mim. Exothermic reaction took place gradually, and temperature of the reaction mixture reached around 105°~110° C. After being maintained at this temperature for 2 hr, it is cooled to room temperature. Water (100 ml) and benzene (100 ml) are added, and the mixture is shaken. Organic layer was separated, washed with water, and concentrated. Removal of excess benzylamine by distillation under reduced pressure gave crude N,N'-dibenzyl-3-aminopyrrolidine (68.9 g, 86.2%), which is distilled under reduced pressure to give N,N'-dibenzyl-3-aminopyrrolidine. Yield 57.6 g (72.1%), bp 185°~189° C./2 mmHg.

$n_D^{20}$ 1.5691. $d_{20}^{20}$ 1.0454.

NMR (CDCl$_3$) δ=7.43 (s, 10H), 3.80 (s, 2H), 3.68 (s, 2H), 1.20~3.57 (m, 8H).

IR (neat) 3300, 1140 cm$^{-1}$ (—NH—).

Elemental analysis (C$_{18}$H$_{22}$N$_2$): Calcd (%): C, 81.16; H, 8.32; N, 10.52. Found (%): C, 80.65; H, 8.48; N, 10.50.

In an autoclave, N,N'-dibenzyl-3-aminopyrrolidine (80 g) dissolved in methanol (300 ml) is stirred for 12 hr at 115° C. over 5% Pd—C catalyst (4 g) under the pressure of hydrogen (20 kg/cm$^2$). After completion of reaction, catalyst is removed by filtration, and the filtrate was carefully concentrated at atmospheric pressure. Distillation of the residual liquid under nitrogen atomosphere gave 3-aminopyrrolidine (16.0 g 61.9%), which boiled at 159°~160° C.

$n_D^{20}$ 1.4897, $SG_{20}^{20}$ 0.9910.

NMR (CDCl$_3$) δ=3.30~3.70 (m, 1H), 2.43~3.23 (m, 4H), 1.13~2.26 (m, 2H), 1.50 (s, 3H).

IR (neat) 3250, 1600, 870 cm$^{-1}$ (—NH$_2$).

Derivatives

3-Aminopyrrolidine dihydrochloride

NMR (DMSO-d$_6$) δ=8.33~10.10 (s, broad, 5H), 3.66~4.23 (m, 1H), 2.93~3.66 (m, 4H), 1.93~2.50 (m, 2H).

IR (KBr) 3200~2800, 1590~1550 cm$^{-1}$ (NH$_3$$^+$).

Elemental analysis (C$_4$H$_{12}$N$_2$Cl$_2$): Calcd. (%): C, 30.21; H, 7.60; N, 17.61. Found (%): C, 29.93; H, 7.63; N, 17.45.

Chlorine content Calcd (%): 44.58 Found (%): 43.74

(b). N,N'-Dibenzyl-3-aminopyrrolidine is prepared by the reaction of various 1,2,4-trisubstituted butanes with benzylamine under similar conditions as those described in EXAMPLE 5a, and is subsequently hydrogenated to 3-aminopyrrolidine. Results are summarized in a following table.

TABLE 1

N,N'—Dibenzyl-3-aminopyrrolidine and 3-aminopyrrolidine from various 1,2,4-trisubstituted butanes

| Starting Material | N,N'—Dibenzyl-3-aminopyrrolidine yield (%) | 3-Aminopyrrolidine yield (%) |
| --- | --- | --- |
| 3.4-Dibromo-1-methanesulfonoxy-butane (bp 137~139/1 mmHg) | 63.7 | 62.0 |
| 1,4-Dibromo-2-methanesulfonoxy-butane (viscous liquid) | 64.0 | 62.0 |
| 1,2,4-Tris(p-toluene-sulfonoxy)butane (mp 91.0~91.7° C.) | 30.7 | 62.5 |
| 1,2-Dibromo-4-chlorobutane (bp 87.5~88.5° C./8 mmHg) | 26.8 | 62.0 |
| 1,2,4-Tris(methane-sulfonoxy)butane (mp 63.5~64.5° C.) | 74.3 | 62.5 |

(c). A mixture of 1,2,4-trichlorobutane (161 g, bp 61.5°~62.0° C./9 mmHg) and benzylamine (1072 g) is gradually heated to 140°~150° C. and stirred for 19 hr at this temperature. After being cooled in ice, benzene (500 ml) is added to the mixture, and precipitates (benzylamine hydrochloride) are filtered. The filtrate is concentrated, and excess benzylamine is removed by distillation under reduced pressure. Distillation of residual liquid gave N,N'-benzyl-3-aminopyrrolidine. Yield 152 g (57.2%), bp 180°~182° C./3 mmHg.

This is hydrogenated at 115° C. over 5% Pd—C (15 g) in methanol (200 ml) under the hydrogen pressure of 20 kg/cm$^2$ for 12 hr. Similar work-up as those described in EXAMPLE 5a gave 3-aminopyrrolidine (30.7 g, 62.5%), which boiled at 159°~160° C.

EXAMPLE 6

N,N'-Bis(1-phenylethyl)-3-aminopyrrolidine and 3-aminopyrrolidine

To a mixture of 1-phenylethylamine (363.5 g) and sodium hydroxide (60 g) in water (120 ml) is added with stirring 1,2,4-tris(methanesulfonoxy)butane (170.2 g, mp 63.5°~64.5° C.).

The mixture is gradually heated to 110° C. and maintained at this temperature for 3 hr, and then cooled to room temperature. To this are added water (50 ml) and benzene (400 ml), and the mixture is shaken. Organic layer was separated, washed with water, and concentrated. Excess 1-phenylethylamine is removed by distillation under reduced pressure. Distillation of the residual liquid gave N,N'-bis(1-phenylethyl)-3-aminopyrrolidine (87.4 g, 59.3%) which boiled at 175°~177° C./2 mmHg.

n$_D$$^{20}$ 1.5552. SG$_{20}$$^{20}$ 1.0201.

NMR (CDCl$_3$) δ=7.30 (s, 10H), 3.53~3.93 (m, 1H), 2.87~3.40 (m, 2H), 1.47~2.83 (m, 7H), 1.40 (d, 3H), 1.28 (d, 3H).

IR (neat) 1150 cm$^{-1}$.

Elemental analysis (C$_{20}$H$_{26}$N$_2$): Calcd (%): C, 81.59; H, 8.90; N, 9.51. Found (%): C, 81.62; H, 8.48; N, 9.52.

In an autoclave, N,N'-bis(1-phenylethyl)-3-aminopyrrolidine (73.6 g) is hydrogenated at 120° C. over 5% Pd—C (15 g) in methanol (200 ml) under the hydrogen pressure of 18 kg/cm$^2$ for 20 hr. After completion of reaction, catalyst is removed by filtration, and the filtrate is carefully concentrated at an atmospheric pressure. Distillation of the residual liquid under nitrogen atmosphere gave 3-aminopyrrolidine (8.8 g, 36.8%), which boiled at 159°~160° C.

Ethylbenzene (bp 136° C.) is readily separated by distillation. NMR and IR spectra of this compound are identical with those obtained in EXAMPLE 5a.

EXAMPLE 7

N,N'-Bis(diphenylmethyl)-3-aminopyrrolidine and 3-aminopyrrolidine

To a mixture of benzhydrylamine (439.8 g) and sodium hydroxide (48 g) in water (100 ml) is added with stirring 1,2,4-tris(methanesulfonoxy)butane (136.1 g, mp 63.5°~64.5° C.).

The mixture is gradually heated to 110° C. and maintained at this temperature for 5 hr, and then cooled to room temperature. To this are added water (50 ml) and benzene (400 ml), and the mixture is shaken. Organic layer was separated, washed with water, and concentrated. Excess benzhydrylamine is removed by distillation under reduced pressure. The residue is dissolved in hot isopropyl alcohol (400 ml), from which N,N'-bis(diphenylmethyl)-3-aminopyrrolidine (73.6 g, 43.9%) crystallized. This is recrystallized from isopropyl alcohol (200 ml). Yield 57.9 g (34.5%). mp. 106°~107° C.

NMR (CDCl$_3$) δ=6.87~7.60 (m, 20H), 4.80 (s, 1H), 4.17 (s, 1H), 300~3.43 (m, 1H), 1.30~2/83 (m, 7H).

IR (KBr) 3350 cm$^{-1}$.

Elemental Analysis (C$_{30}$H$_{30}$N$_2$): Calcd. (%) C, 86.06; H, 7.22; N, 6.69. Found (%) C, 86.33; H, 7.34; N, 6.82.

In an autoclave, N,N'-bis(diphenylmethyl)-3-aminopyrrolidine (50.0 g) is hydrogenated at 105° C. over 5% Pd—C (10 g) in tetrahydrofuran (200 ml) under the hydrogen pressure of 16 kg/cm$^2$ for 3 hr. After completion of reaction, catalyst is removed by filtration, and the filtrate was carefully concentrated. Distillation of the residual liquid under reduced pressure (11 mmHg at 40°~60° C.), gave fractions enriched in 3-aminopyrrolidine, from which pure 3-aminopyrrolidine (bp 159°~160° C., 6.0 g, 58.4%) is obtained by distillation at an atmospheric pressure. Diphenylmethane (bp 264.5° C./760 mmHg) is readily separated.

EXAMPLE 8

N,N'-Dibenzyl-3-aminopyrrolidine dihydrochloride and 3-aminopyrrolidine dihydrochloride N,N'-Dibenzyl-3-aminopyrrolidine (150 g, bp 185°~189° C./2 mmHg, prepared according to the procedure described in EXAMPLE 5a) is added dropwise with stirring and ice cooling, to ethanol (600 ml) solution of hydrogen chloride (42 g), and the mixture is stirred for 2 hr. N,N'-Dibenzyl-3-aminopyrrolidine dihydrochloride precipitated, which is collected by suction filtration, and recrystallized from ethanol (880 ml).

Yield 184.8 g (96.8%), mp 235.2°~236.8° C. (dec.).

Chlorine Content ($C_{18}H_{24}N_2Cl_2$): Calcd (%) 20.90. Found (%) 20.86.

In an autoclave, N,N'-dibenzyl-3-aminopyrrolidine dihydrochloride (85 g) is hydrogenated at 35° C. over 5% Pd—C (8.5 g) in a mixed solvent of methanol (160 ml) and water (40 ml) under the hydrogen pressure of 10 kg/cm² for 5 hr. After completion of reaction, catalyst is removed by filtration, and the filtrate is concentrated. Ethanol (100 ml) is added to the residue, and white crystalline solid of 3-aminopyrrolidine dihydrochloride is collected by suction filtration. Yield 35.4 g (88.9%).

NMR (DMSO-$d_6$) $\delta = 8.33 \sim 10.10$ (s, broad, 5H), $3.66 \sim 4.23$ (m, 1H), $2.93 \sim 3.66$ (m, 4H), $1.93 \sim 2.50$ (m, 2H).

IR (KBr) $3200 \sim 2800$, $1590 \sim 1550$ cm$^{-1}$(—NH$_3^+$).

Elemental analysis ($C_4H_{12}N_2Cl_2$): Calcd (%): C, 30.21; H, 7.60; N, 17.61. Found (%): C, 29.93; H, 7.63; N, 17.45.

Chlorine content: Calcd (%): 44.58. Found (%): 43.74.

What is claimed is:

1. A process for preparing a compound of 3-aminopyrrolidine having the formula:

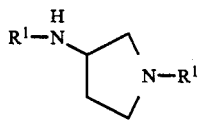

in which R¹ is hydrogen, which comprises reacting 1,2,4-trisubstituted butane having the formula:

XCH₂CHYCH₂CH₂Z in which X, Y and Z each is a halogen or —OR, R being an alkylsulfonyl having 1 to 6 carbon atoms in the alkyl or an arylsulfonyl in which the aryl is phenyl or a phenyl substituted by methyl, methoxy, nitro or a halogen, with ammonia.

2. A process for preparing a compound of 3-aminopyrrolidine having the formula:

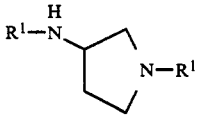

in which R¹ is an alkyl having 1 to 20 carbon atoms, phenyl, an aralkyl having 1 or 2 carbon atoms in the alkylene and 1 or 2 phenyls in the aryl or —CHR²R³, R² being phenyl or a phenyl substituted by methyl, methoxy, a halogen or nitro, R³ being hydrogen, an alkyl or phenyl, which comprises reacting 1,2,4-trisubstituted butane having the formula:

XCH₂CHYCH₂CH₂Z

in which X, Y and Z each is a halogen or —OR, R being an alkysulfonyl having 1 to 6 carbon atoms in the alkyl or an arylsulfonyl in which the aryl is phenyl or a phenyl substituted by methyl, methoxy, nitro and a halogen with a primary amine having the formula:

R¹NH₂

in which R¹ is as defined above.

3. A process as claimed in claim 2, in which R¹ is benzyl.

4. A process as claimed in claim 2, in which R¹ is —CHR²R³, R² being phenyl, R³ being hydrogen, methyl or phenyl.

5. A process for preparing 3-aminopyrrolidine comprising catalytically hydrogenating a compound of 3-aminopyrrolidine having the formula:

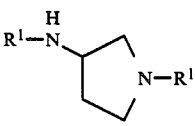

in which R¹ is an alkyl having 1 to 20 carbon atoms, phenyl, an aralkyl having 1 or 2 carbon atoms in the alkylene and 1 or 2 phenyls in the aryl or —CHR²R³, R² being phenyl or a phenyl substituted by methyl, methoxy, a halogen or nitro, R³ being hydrogen, an alkyl or phenyl or, salts of the compound, with a protonic acid.

* * * * *